United States Patent [19]

Bassett et al.

[11] Patent Number: 4,698,116

[45] Date of Patent: Oct. 6, 1987

[54] BOLUS ASSEMBLY APPARATUS

[75] Inventors: Gregory S. Bassett, Indianapolis; Robert L. Bollman, Mooresville, both of Ind.

[73] Assignee: Eli Lilly and Company, Indianapolis, Ind.

[21] Appl. No.: 839,636

[22] Filed: Mar. 14, 1986

[51] Int. Cl.$^4$ .................. B29C 33/10; B32B 31/06
[52] U.S. Cl. ............................ 156/423; 156/294; 156/578
[58] Field of Search ............... 156/294, 423, 578, 292, 156/228, 145, 146; 264/46.6, 262, 35, 46.5, 275

[56] References Cited

U.S. PATENT DOCUMENTS

| | | | |
|---|---|---|---|
| 3,184,362 | 5/1965 | Litsky | 156/294 |
| 3,607,494 | 9/1971 | Rowland | 264/262 |
| 4,288,058 | 9/1981 | Inman | 264/262 |
| 4,589,950 | 5/1986 | Sekavec | 156/578 |

Primary Examiner—Donald E. Czaja
Assistant Examiner—J. Davis

Attorney, Agent, or Firm—Barnes & Thornburg

[57] ABSTRACT

An assembly apparatus is disclosed for assembling a first element having opposed end surfaces within a second element so as to leave the end surfaces exposed subsequent to the application of an adhesive material. The apparatus includes a pair of elastomeric seals, each seal having an axially inner surface for contacting an end surface of the first element, the edge of the axially internal surface acting to position the end surfaces of the first element wholly within the edge of the internal surface. Each seal also includes a step spaced a preselected distance outside of the internal surface edge for positioning the second element generally coaxially with respect to the first element. The lower seal includes apertures for permitting the introduction of adhesive material between the first and second elements while the upper seal includes apertures to permit venting of the space between the first and second elements, the venting apertures leading to a reservoir for receiving any overfill of the adhesive material.

9 Claims, 3 Drawing Figures

BOLUS ASSEMBLY APPARATUS

The present invention relates generally to assembly apparatus and methods employing adhesive bonding to assemble two elements, particularly a first element having opposed end surfaces within a second element so as to leave the end surfaces of the first element exposed. The apparatus has particular utility for assembling a pharmaceutical formulation for use in animal husbandry so as to provide a delivery device for the sustained delivery of a drug to a ruminant animal over a long period of time.

The desirability of the controlled release of therapeutic agents including weight gain promoting agents to ruminants and a discussion of suitable compositions is found in Kleber et al., U.S. Pat. No. 4,333,919. That patent discloses a biodegradable controlled release formulation of a growth-promoting and feed utilization enhancing agent intimately dispersed throughout a copolymer which is subject to degradation over a long period of time of up to about two hundred days. The controlled release formulation is formed into a solid mass for oral administration to a ruminant. That patent discloses in Examples 8 and 10 that a biodegradable controlled release formulation was packed into a steel cylinder. The purpose of the steel cylinder is to provide the assembly with sufficient weight so as to remain in the reticulo-rumen of the ruminant during the period of biodegradation. The size of the steel cylinder may vary as a function of the size of the animal to which the assembly is to be administered.

Simpson, British Patent No. 2,059,767, discloses a quantity of drug-containing polymeric matrix inside a steel cylinder of between 1 and 2 mm thick. A physical retaining means in the form of a series of grooves is provided on the inner wall of the cylinder so as to retain the drug containing core within the cylinder. It is important that the drug containing core and the cylinder wall be contiguous such that rumen fluids do not flow into the interface therebetween since such action would tend to loosen the formulated drug core and increase the exposed surface area of the core, thus delivering excessive amounts of the drug to the animal. Such excessive doses can, in some cases, be lethal to the animal.

To ensure that rumen fluids do not flow into the interface between the core and the steel cylinder, Simpson discloses that the inner surface of the cylinder is coated, prior to the addition of the core, with a metal such as nickel, magnesium, silver, or aluminum, or other suitable food-grade enamel or lacquer such as epoxy-phenolic resins, or with a plastic so as to decrease or eliminate any depolymerization of the surface of the drug core which contacts the metal cylinder. Subsequent to the coating of at least the interior surface of the cylinder with one of the aforementioned materials, the drug containing core is extruded or compressed and fused into the interior of the steel cylinder.

While the Kleber and Simpson apparatus performs adequately, the method of assembly is unduly slow and, on occasion, results in voids along the surface of the core leading to undesirable exposure of increased surface areas, thus permitting the delivery of excessive amounts of active drug to the animal.

An object of the present invention is the development of an assembly method more expeditious and reliable than that previously known for the assembly of drug delivery devices particularly adapted for use with ruminants. In a broader sense, the purpose of the present invention is to provide an expeditious method and apparatus for the assembly of a first element having opposed end surfaces within a second element so as to leave only the end surfaces of the first element exposed.

In accordance with the present invention, a supply of first elements is provided, the first elements having opposed end surfaces which are generally parallel. The supply of such first elements may be by way of continuous extrusion of a ribbon or rod of the material followed by periodic severing or cutting of the ribbon or rod into first elements having substantially uniform length. In the particular application envisioned by the present invention, the first elements can be formed of a continuous or semicontinuous extrusion of rods of uniform diameter of the drug-containing formulation followed by cutting the rods to a substantially uniform length.

A supply of second elements is also provided, the second elements being preferably sections of steel tubing cut to a substantially uniform length slightly less than the length of the first elements. The interior diameter of the second elements is slightly greater than the exterior diameter of the first elements such that the first elements can be quickly and easily received within the second elements, and, if aligned, a uniform space can be achieved between the interior surface of the second element and the exterior surface of the first element.

A pair of seals is provided, each seal having an axially internal surface for contacting an end surface of the first element and means for aligning the first and second elements with respect to each other. The axially internal surface and aligning means are generally formed by a cup-shaped recess including a radially innermost surface bounded by an edge for contacting the end surface of the first element, and a step radially spaced outside said edge for positioning the second element. At least one aperture is provided in each seal between the edge of the axially internal surface and the step.

During assembly, an end of one of the second elements is positioned on a first of the seals. A first element is then inserted within the second element so as to bring an end of the first element in contact with the first of the seals. A second of the seals is then applied to the remaining ends of the first and second elements. An end-to-end pressure is then applied to the seals which effects alignment of the first and second elements, generally coaxially with respect to each other. A cementitious material or adhesive is then introduced into the space between the first and second elements through at least one of the apertures in one of the seals. As the adhesive is introduced, air escapes from between the first and second elements through the aperture provided in the second seal. The adhesive is permitted to set and the end seals are then removed, thereby exposing the end surfaces of the first element previously contacted by the axially internal surfaces of the seals.

One feature of the present invention is the use of end seals having a step radially spaced outside the edge of the axially inner surface contacting the end surface of the first element which, together with the use of first and second elements of slightly different length, has the advantage of achieving an automatic coaxial alignment of the first and second elements merely by the application of an axial pressure. Another feature of the present invention is the construction of such seals from a soft elastomeric polysiloxane polymer which has the advantage of conforming to minor variations in the end surfaces of the first elements as well as a resistance to bonding to a wide variety of adhesives which permits the release of the seals from the delivery device once assembled.

Additional features and advantages of the invention will become apparent to those skilled in the art upon consideration of the following detailed description of a preferred embodiment exemplifying the best mode of carrying out the invention as presently perceived. The detailed description particularly refers to the accompanying figures in which.

Figure 1:
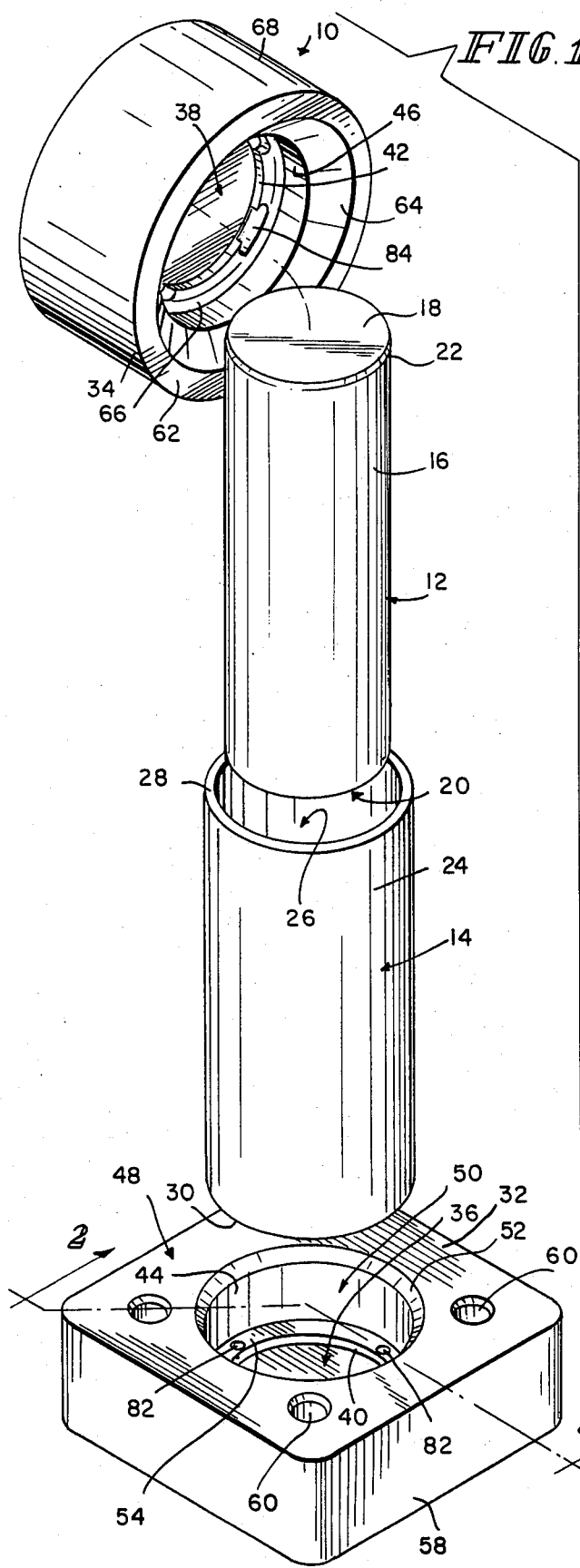
FIG. 1 is an exploded view showing the assembly of a first core element within a cylindrical second element and the two end seals.

Assembly apparatus 10 for adhesively bonding a first element 12 within a second element 14 is shown in an exploded view in FIG. 1. The first element 12 is shown to be a generally right cylindrical solid having an outer surface 16 and parallel ends 18 and 20 bounded by radiused or chamfered edges 22. Of particular interest is a first element 12 composed essentially of a polyglycolic acid matrix having uniformly dispersed therein a drug such as monensin for oral administration to ruminants.

The second element is shown to be a thin right circular cylinder having an outside wall 24, an inside wall 26, and annular ends 28 and 30. The inside diameter of the second element 14 defined by the inside wall 26 is selected to be greater than the outside diameter of the first element 12 defined by wall 16. The second element 14 is in the present invention preferably constructed of low carbon steel or stainless steel. The thickness of the tubing is preferably in the range of about 1 to 4 mm depending upon the diameter of the device to be constructed.

While the second element is shown in the preferred embodiment to be a right circular cylinder, other forms and shapes can advantageously use the present inventive method including square, triangular, or oval tubes. Likewise, the shape of the first element 12 need not be a right cylindrical solid but may have other shapes which may or may not conform to the shape of the surrounding second element, the only limitation being that the first element 12 has two opposed faces 18 and 20 intended to be exposed subsequent to their assembly in accordance with the present invention.

The assembly apparatus 10 includes a lower seal 32 and an upper seal 34, each seal having an axially internal surface 36, 38 for contacting the end surfaces 20, 18 of the first element 12, respectively. An edge defining means in the form of a lip 40 and 42 forms a boundary for the axially inner surfaces 36 and 38, respectively. A step defined by a radially inwardly facing axial surface 44 and 46 spaced outside the edge 40 and 42 receives and positions the outer surface 24 of the second element 14.

The lower seal 32 is further defined by an upper surface 48 having a generally cup-shaped recess 50. The cup-shaped recess is defined by an inwardly facing circular chamfer 52 connecting the upper surface 48 to the radially inwardly facing cylindrical surface 44. At the bottom of the inwardly facing surface 44 is an upwardly facing land 54 adapted to contact end 30 of the second element 14. The inner edge of land 54 is defined by the upraised edge 40 of the axially inner surface 36.

The lower seal 32 further comprises a lower surface 56 parallel to the upper surface 48 and an outer perimeter 58 connecting surfaces 48 and 56. The upper and lower surfaces 48 and 56 are also connected by a series of openings 60 shown in both FIGS. 1 and 2. The lower seal further includes a reinforcing plate 62 situated between the lower surface 56 and the axially internal surface 36 for reinforcing and rigidifying the lower seal. The reinforcing plate 62 is preferably composed of steel while the remainder of the lower seal 32 is preferably composed of a polysiloxane polymer having a durometer of between about 15 and 40 Shore A. The upper seal 34 is preferably composed of the same polymer.

The upper seal 34 is shown to include a lower surface 62 and a radially inwardly facing chamfer 64 connecting the lower surface 62 to the radially inwardly facing surface 46. At the top of surface 46 is land 66, the inner edge of which defines the edge of the axially internal surface 38. The upper seal 34 further includes an outer perimeter 68 connecting the lower surface 62 to an upper surface 70 shown best in FIG. 2. The upper surface 70 includes a ring-shaped trough 72 defined by a radially outer surface 74 and a radially inner surface 76, the radially inner surface defining an island 78 and the radially outer surface 74 and outer perimeter 68 defining an outer margin 80. The top surface of the outer margin 80 and island 78 lie in a common plane defining the top surface 70.

The lower seal 32 includes a plurality of apertures 82 for permitting the introduction of adhesive material between the first and second elements. The apertures 82 are situated such that the aperture passes from the lower surface 56 to the land 54 of the lower seal 32. The upper seal includes venting means 84 for venting air from between the first and second elements as adhesive material is introduced between the first and second elements. The venting means 84 comprises a plurality of apertures leading from land 66 to the ring-shaped trough 72. The ring-shaped trough 72 functions as a reservoir for receiving excess adhesive material which may pass through the vent apertures 84 after completely filling the space between the first and second elements.

Figure 2:
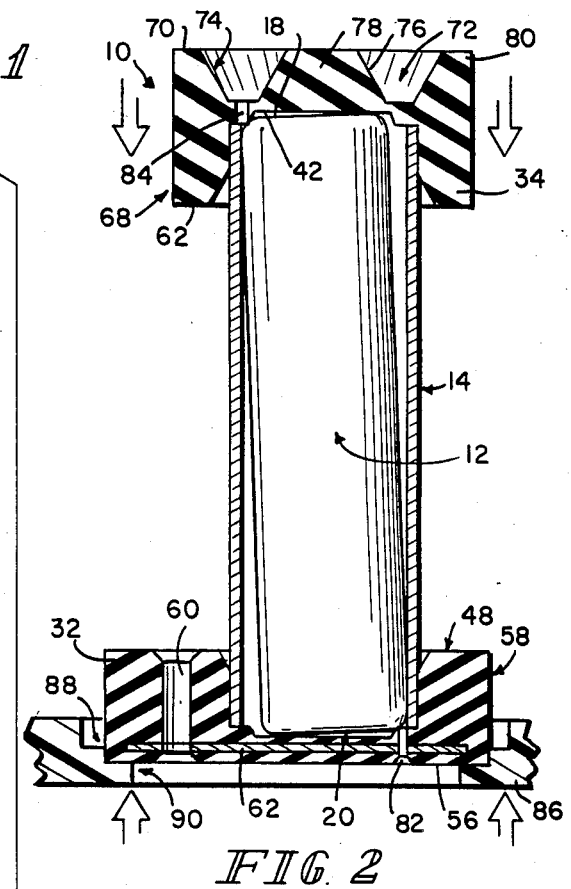
FIG. 2 is a sectional view showing a representative preliminary placement of the first element within the second element prior to any axial force being applied on the end seals.
Figure 3:
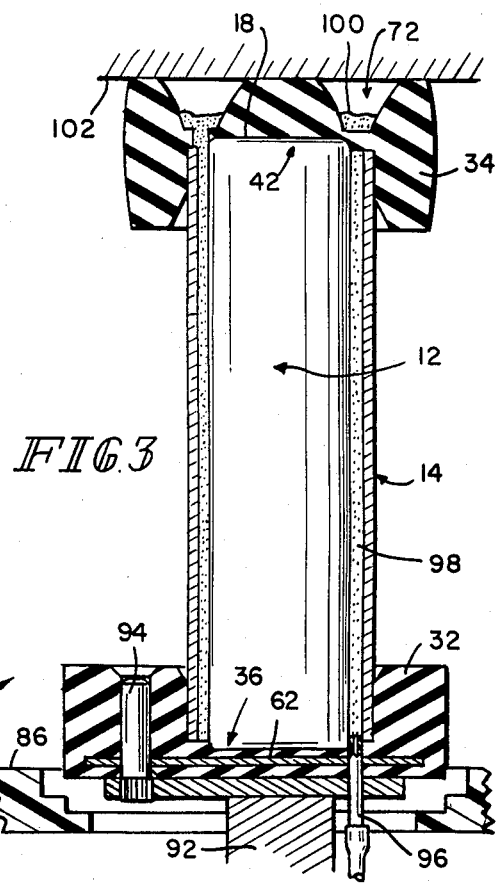
FIG. 3 is a sectional view showing the application of an axial force together with the introduction of an adhesive between the first and second elements.

In operation, the lower seal 32 is positioned on a carrier frame 86 shown in part in FIGS. 2 and 3. The carrier frame may be of any convenient external shape and can be connected to other similar frames for holding and transporting the assembly apparatus of the present invention from station to station during the assembly herein contemplated. The frame 86 should include an upper surface including a step 88 for reliably positioning the lower seal 32 with respect to the frame 86. The carrier frame should also include a central opening 90 to permit access to the lower surface 56 of the lower seal as hereinafter described.

After the lower seal 32 is situated within the carrier frame 86, the second element is inserted into the cup-shaped recess 50 such that the outer surface 14 of the second element contacts the radially inwardly facing surface 44, and the lower end 30 of the second element 14 contacts land 54 of the lower seal. A first element 12 is then deposited within the second element 14. The first element 12 may be slightly skewed within the second element 14 as illustrated in FIG. 2. The upper seal 34 is then situated on the upper end of the assembly as shown in FIG. 2. The seals are then subjected to an axial pressure. The axial pressure causes the edge defining means 40 and 42 to apply a torque to the first element 12 causing the first element to be coaxially aligned within the second element 14. This coaxial alignment of the first element 12 also ensures that the end surfaces 18 and 20 come in smooth continuous contact with the radially inner surfaces 38 and 36 of the upper and lower seals 34 and 32, respectively.

An adhesive introducing means 92 shown in FIG. 3 is then inserted into the lower seal 32. The adhesive introducing means includes one or more pins 94 adapted to be received in openings 60 of the lower seal. The adhesive introducing means also includes at least one hollow injecting means 96 connected to a source of adhesive (not shown) which is received in one or more apertures 82 in the lower seal. With the assembly experiencing axial pressure applied between the adhesive introducing means 92 and an abutting means 102, an adhesive 98 is introduced into the space between the first element 12 and second element 14, the amount of adhesive introduced being controlled such that the entirety of the space 98 is filled as well as a lowermost portion 100 of circular trough 72 as shown in FIG. 3.

Of particular utility are adhesives generally referred to as "hot-melts" which are typically thermoplastic copolymers such as ethylene vinyl acetate, polyethylene and polyamide resins. Further information concerning hot-melt adhesives is available from Chapter 30 of *Handbook of Adhesives,* Irving Skeist, Ed., 2nd edition, VanNostrand Reinhold (1977). The hot-melt adhesive is applied by heating and injecting it under modest pressure. The adhesive is then permitted to set and the assembly 10 is removed from the carrier frame 86. The lower and upper seals are then removed from the ends of the combined device formed by first element 12, second element 14, and the intervening adhesive layer. The removal of seals 32 and 34 exposes the end faces 18 and 20 of the first element 12. Any residual adhesive 98 is then removed from the seals 32 and 34, and the seals are recycled for subsequent use in the assembly of another similar device.

Although the invention has been described in detail with reference to the illustrated preferred embodiment, variations and modifications exist within the scope and spirit of the invention as described and as defined in the following claims.

What is claimed is:

1. Assembly apparatus for adhesively bonding a first element having opposed end surfaces within a second element so as to leave the end surfaces exposed, the apparatus comprising: a lower seal and an upper seal, each seal composed of a soft, elastomeric polymer having an axially internal surface for contacting the end surface of the first element, positioning means defining an edge of the axially internal surface for positioning said end surface wholly within said edge, and a step radially spaced outside said edge for positioning the second element at a preselected distance from the first element, at least one of the upper and lower seals including means for introducing cementitious material between said edge and said step, and at least one of the seals including a reinforcing plate situated adjacent to said axially internal surface for reinforcing the seal.

2. The assembly apparatus of claim 1 wherein at least one of the upper and lower seals includes venting means for venting air from between the first and second elements as adhesive material is introduced therebetween.

3. The assembly apparatus of claim 2 further comprising reservoir means connected to the venting means for receiving excess adhesive material.

4. The assembly apparatus of claim 1 further comprising carrier means for carrying one of the upper and lower seals including an aperture permitting access to the means for introducing adhesive material.

5. The assembly apparatus of claim 4 further comprising abutting means for abutting an outer surface of the seal not carried by the carrier means to permit compression loading of the seals.

6. The assembly apparatus of claim 1 wherein the polymer consists essentially of polysiloxane polymer having a durometer of between about 15 and 40 Shore A.

7. A lower seal for an assembly apparatus for adhesively bonding a first element having a lower end surface within a second element so as to leave the end surface exposed, the lower seal comprising: an upper surface having a cup-shaped recess for receiviqg the first and second elements, the cup-shaped recess including a radially innermost surface bounded by an edge for contacting the end surface of the first element, a step radially spaced outside said edge for positioning the second element, at least one aperture between the edge and step for directing adhesive material between the first and second elements, a lower surface parallel to said upper surface and below said radially innermost surface, an outer perimeter connecting the upper surface and the lower surface, and a reinforcing plate situated between the lower surface and the radially innermost surface for reinforcing the lower seal.

8. The lower seal of claim 7 further comprising at least one opening in the lower surface for receiving a guide pin to guide the introduction of the adhesive material into said at least one aperture.

9. An assembly apparatus for adhesively bonding a first element having a lower end surface to a second element so that the first element is rigidly fixed within the second element so as to leave the end surface exposed, the assembly apparatus consisting essentially of a lower seal having an upper surface having a cup-shaped recess for receiving the first and second elements, the cup-shaped recess including a radially innermost surface for contacting the end surface of the first element and an upstanding boundary edge circumcribing the radially innermost surface for receiving and positioning the first element, a step radially spaced outside said upstanding boundary edge for positioning the second element, at least one aperture between the upstanding boundary edge and step for directing adhesive material between the first and second elements, the adhesive material permanently bonding the first and second elements to one another.

* * * * *

UNITED STATES PATENT AND TRADEMARK OFFICE
CERTIFICATE OF CORRECTION

PATENT NO. : 4,698,116

DATED : October 6, 1987

INVENTOR(S) : Bassett et al.

It is certified that error appears in the above-identified patent and that said Letters Patent is hereby corrected as shown below:

In Col. 6, line 52, delete "circumcribing" and insert --circumscribing--.

Signed and Sealed this

Fifteenth Day of March, 1988

Attest:

DONALD J. QUIGG

Attesting Officer

Commissioner of Patents and Trademarks